US006471942B1

(12) United States Patent
Miller et al.

(10) Patent No.: US 6,471,942 B1
(45) Date of Patent: Oct. 29, 2002

(54) IMAGING AND TREATMENT METHOD FOR BODY

(75) Inventors: Michael B. Miller, Christiansburg; Kent A. Murphy, Troutville; Harry C. Dorn, Blacksburg; Steven A. Stevenson, Blacksburg; Janice P. Stevenson, Blacksburg; Shufang Luo, Blacksburg, all of VA (US)

(73) Assignee: Luna Innovations, Inc., Blacksburg, VA (US)

( * ) Notice: Subject to any disclaimer, the term of this patent is extended or adjusted under 35 U.S.C. 154(b) by 0 days.

(21) Appl. No.: 09/839,797

(22) Filed: Apr. 20, 2001

Related U.S. Application Data

(60) Provisional application No. 60/198,697, filed on Apr. 20, 2000.

(51) Int. Cl.$^7$ ................................................ A61K 49/00
(52) U.S. Cl. ........................ 424/9.1; 534/15; 424/1.11
(58) Field of Search ................................ 534/7, 10–16; 424/1.11, 9.1, 9.2, 1.65, 1.69, 9.3, 9.4, 9.5, 9.6

(56) References Cited

U.S. PATENT DOCUMENTS

| | | | |
|---|---|---|---|
| 5,547,748 A | * | 8/1996 | Ruoff et al. ................. 428/323 |
| 5,688,486 A | | 11/1997 | Watson et al. |
| 5,717,076 A | | 2/1998 | Yamamoto et al. |
| 5,869,626 A | | 2/1999 | Yamamoto et al. |
| 6,303,760 B1 | * | 10/2001 | Dorn et al. ..................... 534/11 |

OTHER PUBLICATIONS

Lon J. Wilson, "Medical Applications of Fullerenes and Metallofullerenes," *Interface*, Winter 1999, p. 24–28, The Electrochemical Society.

S. Stevenson et al., "Small–Bandgap Endohedral Metallofullerenes in High Yield and Purity," *Nature*, Sep. 2, 1999, p. 55–57, vol. 401.

S. Stevenson et al., "A Stable Non–Classical Metallofullerene Family," *Nature*, Nov. 23, 2000, p. 427–428, vol. 408.

Chun–Ru Wang et al., "$C_{66}$Fullerence Encaging A Scandium Dimer", *Nature*, Nov. 23, 2000, p. 426, vol. 408.

Haruhito Kato et al., "Evaluation of Water–Soluble Metallofullerenes for MRI Contrast Agents," *Abstracts of the 20$^{th}$ Fullerene General Symposium*, Jan. 22–23, 2001, p. 38.

Kymbr L. S. Lawrence and Garyl J. Ehrhardt, "Fullerene Radiopharmaceuticals? High–Flux Neutron Irradiation Study of $C_{60}$," *Electrochemical Society Proceedings*, Date unknown, p. 66–71, vol. 95–10.

Dawson W. Cagle et al., "Synthesis, Characterization and Neutron Activation of Holmium Metallofullerenes," *Journal of American Chemical Society*, 1996, p. 8043–8047, vol. 118.

Dawson W. Cagle et al., "In Vivo Studies of Fullerene –Based Materials Using Endohedral Metallofullerene Radiotracers," *Proceedings of the National Academy of Science*, Apr. 1999, p. 5182–5187, vol. 96.

Tatiana Da Ros and Maurizio Prato, "Medicinal Chemistry with Fullerenes and Fullerene Derivatives," *Chemical Communications*, 1999, p. 663–669.

* cited by examiner

*Primary Examiner*—Dameron L. Jones
(74) *Attorney, Agent, or Firm*—Joy L. Bryant

(57) ABSTRACT

A method for imagining and treating a body employing at least one trimetallic nitride template endohedral metallofullerene compound is disclosed. The compound has at least one diagnostic and at least one treatment atom encapsulated within a fullerene cage. The two atoms are different from each other. The compound is administered into a body, traced, and allowed to react at a targeted area of the body.

15 Claims, No Drawings

IMAGING AND TREATMENT METHOD FOR BODY

CROSS-REFERENCE TO RELATED APPLICATIONS

This application claims the benefit of U.S. Provisional Application No. 60/198,697, entitled, "Endohedral Metallofullerene Compounds," filed Apr. 20, 2000, hereby incorporated by reference in its entirety.

FIELD OF THE INVENTION

This application is related to imaging and treatment methods for a body. In particular, it relates to an imaging and treatment method which employs trimetallic nitride template endohedral metallofullerene compounds.

BACKGROUND OF THE INVENTION

Endohedral metallofullerenes are fullerene structures (carbon clusters) with closed topologies, encapsulating metallic or non-metallic atoms. Typically, metallofullerenes are prepared by impregnating graphite rods with a metal salt and annealing at approximately 1000° C. Before the rods burn, a small amount of metallofullerene is produced in the soot. The soot is then extracted with solvents such as $CS_2$ or o-dichlorobenzene, followed by high performance liquid chromatography (HPLC) to obtain pure samples of the endohedral metallofullerenes. $M@C_{82}$ is the most predominant species extracted. However, multiple metal-atom species such as Y, Ho, or Er dimers, and Sc trimer have also be formed and extracted. Although a broad range of endohedral species containing from 60 to 200 carbon atoms and one or more metal atoms have been formed, most are insoluble and, thus, are not useful for biological applications. Typical metal atoms that are encapsulated are alkali metal, alkaline earth metal, Sc, Y, U or a lanthanide metal. The lanthanide elements have been found to be useful for diagnostic and therapeutic medicine, making them attractive for applications in medicine.

Current synthesis methods make it difficult to perform detailed studies of the properties associated with endohedral metallofullerenes because the typical yields are less than 0.5%. In addition, multiple endohedral fullerene isomers are produced using these synthetic methods.

Stevenson et al. ("Small-bandgap endohedral metallofullerenes in high yield and purity," *Nature*, Sep. 2, 1999, Vol. 401, pp. 55–57) describe a technique where the introduction of small amounts of nitrogen into an electric-arc reactor allows for the efficient production of a new family of stable endohedral fullerenes encapsulating trimetallic nitride clusters, $Er_2$—$SC_3$—$N@C_{80}$ (x=0–3). The trimetallic nitride template process generates milligram quantities of product containing 3–5% $Sc_3N@C_{80}$, allowing isolation of the material and determination of the crystal structure, optical and electronic properties. The $Sc_3N$ moiety is encapsulated in a highly symmetric, icosahedral $C_{80}$ cage, which is stabilized as a result of charge transfer between the nitride cluster and the fullerene cage. Their method provides access to a range of small-bandgap fullerene materials whose electronic properties can be tuned by encapsulating nitride clusters containing different metals and metal mixtures. Although Stevenson et al. have described a new type of endohedral metallofullerene that contains anywhere from 0–3 atoms, they fail to provide a specific use for these materials. Moreover, since the atoms contained within the fullerene cage are all the same, the versatility of the compounds is greatly restricted.

An object of the present invention is to provide a method for imaging and treating an area of a body which employs at least one trimetallic nitride template endohedral metallofullerene compound having at least one diagnostic atom and at least one treatment atom encapsulated within a fullerene cage such that the diagnostic atom is different from the treatment atom.

Another object of the present invention is to provide a method for imaging and treating an area of the body that is versatile and amenable to many different applications in a body.

SUMMARY OF THE INVENTION

The aforementioned objects were accomplished by the present invention which is directed toward a method for imaging and treating an area of a body. The method comprises the steps of providing at least one trimetallic nitride template endohedral metallofullerene compound. The metallofullerene compound has at least one diagnostic atom and at least one treatment atom encapsulated within a fullerene cage. The diagnostic atom is different from the treatment atom. The trimetallic nitride template endohedral metallofullerene compound is administered into a body and is traced to an area of the body. The treatment atom is then permitted to react in the area of the body. The novel feature of this invention is that it employs a mixed metal cluster encapsulated within the fullerene cage. Since at least two of the three metals are different from each other, it is possible to have both a diagnostic and a treatment atom contained within the same fullerene cage.

Additional objects and advantages of the invention will be set forth in part in the description which follows, and in part will be obvious from the description, or may be learned by practice of the invention. The objects and advantages of the invention will be obtained by means of instrumentalities in combinations particularly pointed out in the appended claims.

DETAILED DESCRIPTION OF THE PREFERRED EMBODIMENTS

The method of the present invention is useful in applications where it is desirable to not only diagnose or image a certain area of a body but to treat a targeted area in the body as well. The mixed metal cluster encapsulated within the fullerene cage makes it possible to diagnose and treat a targeted region in the body. The method of the present invention comprises providing at least one trimetallic nitride template endohedral metallofullerene compound having at least one diagnostic atom and at least one treatment atom encapsulated within a fullerene cage. Any fullerene cage known to one of skill in the art may be used to encapsulate the diagnostic and treatment atoms, and in particular the fullerene cage is selected from the group consisting of: a $C_{68}$ cage, a $C_{78}$ cage, and a $C_{80}$ cage. In a most preferred embodiment of the invention, the fullerene cage is a $C_{80}$ cage.

It is necessary that the diagnostic atom and the treatment atom have different chemical compositions from one another. For example, the diagnostic atom is selected from the group consisting of: yttrium, erbium, europium, holmium, and gadolinium. In a most preferred embodiment of the invention, the diagnostic atom is gadolinium. In some instances, there may be first and second diagnostic atoms encapsulated within the fullerene cage. In this instance, the two diagnostic atoms are different from each other as well as the treatment atom. In a preferred embodiment, the first and second diagnostic atoms are selected from the group consisting of: yttrium, erbium, europium, holmium, and gadolinium. In a most preferred embodiment, the first diagnostic atom is gadolinium and the second diagnostic atom is europium. These diagnostic atoms differ from that of the treatment atom. Any treatment atom known to those of skill in the art may be used. Typically the treatment atom is a radioactive isotope having a half-life ranging from about one hour to about 72 hours. Various examples of these isotopes include but are not limited to: holmium, actinium, ruthenium, and yttrium. Preferably, the treatment atom is holmium. In a most preferred embodiment of the invention, the treatment atom is holmium and the diagnostic atom is gadolinium.

The trimetallic nitride template endohedral metallofullerene compound of the present invention may be modified to enhance absorption of the compound in the body and in target tissues. This is accomplished by attaching at least one functional group to the fullerene cage. For example to enhance the absorption of the trimetallic nitride template endohedral metallofullerene compound in the body, a functional group selected from the group consisting of: an aminosubstituted group; a carboxyl group; a hydroxyl group; a polyethylene glycol complex; carbohydrates; amino acids; proteins; nucleic acids; markers; and an antibody is attached to the fullerene cage. Typical carbohydrates include but are not limited to: sugars and polysaccharides. Various proteins include but are not limited to: proteins having hydrophilic moieties; proteins having hydrophobic moieties; antigens; antibodies; and receptors. Any nucleic acids known to those of ordinary skill in the art may also be employed and more specifically, deoxyribonucleic acids, ribonucleic acids, and oligonucleotides may be used.

Alternatively, because of the significant difference in the size ratio, a plurality of trimetallic nitride template endohedral metallofullerene compounds may be attached to a single antibody and introduced into the body in that form.

In furtherance of the method of the present invention, the trimetallic nitride template endohedral metallofullerene compound is administered into a body. Any method known to those of skill in the art may be used to administer the compound. Typically, the compound is injected into the body, Once administered, the trimetallic nitride template endohedral metallofullerene compound is traced to an area of the body. Any method known to those of skill in the art may be used to trace the compound. For example, a typical method is magnetic resonance imaging, Once the compound has reached its target site, it is allowed to react in that area of the body. As a further embodiment of the invention, the trimetallic nitride template endohedral metallofullerene compound is identified and recovered from the body.

The above description is only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed is:

1. A method for imaging and treating an area of a body, the method comprising the steps of:
   a) providing at least one trimetallic nitride template endohedral metallofullerene compound having at least one diagnostic atom and at least one treatment atom encapsulated within a fullerene cage, wherein the diagnostic atom is different from the treatment atom;
   b) administering the trimetallic nitride template endohedral metallofullerene compound into a body;
   c) tracing the trimetallic nitride template endohedral metallofullerene compound to an area of the body; and
   d) allowing the treatment atom to react in the area of the body.

2. A method according to claim 1, wherein the fullerene cage is selected from the group consisting of: a $C_{68}$ cage, a $C_{78}$ cage, and a $C_{80}$ cage.

3. A method according to claim 2, wherein the fullerene cage is a $C_{80}$ cage.

4. A method according to claim 1, wherein the diagnostic atom is selected from the group consisting of: yttrium, erbium, europium, holmium, and gadolinium.

5. A method according to claim 4, wherein the diagnostic atom is gadolinium.

6. A method according to claim 1, wherein the trimetallic nitride template endohedral metallofullerene comprises a first diagnostic atom and a second diagnostic atom wherein the first diagnostic atom is different from the second diagnostic atom.

7. A method according to claim 6, wherein the first diagnostic atom and the second diagnostic atom are selected from the group consisting of: yttrium, erbium, europium, holmium, and gadolinium.

8. A method according to claim 7, wherein the first diagnostic atom is gadolinium and the second diagnostic atom is europium.

9. A method according to claim 1, wherein the treatment atom is a radioactive isotope having a half-life ranging from about one hour to about 48 hours.

10. A method according to claim 9, wherein the treatment atom is holmium.

11. A method according to claim 10, wherein the diagnostic atom is gadolinium.

12. A method according to claim 1, wherein the trimetallic nitride template endohedral metallofullerene compound further comprises at least one functional group attached to the fullerene cage, wherein the functional group enhances absorption of the trimetallic nitride template endohedral metallofullerene compound in the body.

13. A method according to claim 12, wherein the functional group is selected from the group consisting of: an aminosubstituted group; a carboxyl group; a hydroxyl group; a polyethylene glycol complex; carbohydrates; amino acids; proteins, nucleic acids; markets; and an antibody.

14. A method according to claim 1, wherein a plurality of trimetallic nitride template endohedral metallofullerene compounds are attached to an antibody.

15. A method for imaging and treating an area of a body, the method comprising the steps of:
   a) providing at least one trimetallic nitride template endohedral metallofullerene compound having at least one diagnostic atom and at least one treatment atom encapsulated within a fullerene cage, wherein the diagnostic atom is different from the treatment atom;
   b) administering the trimetallic nitride template endohedral metallofullerene compound into a body;
   c) tracing the Bimetallic nitride template endohedral metallofullerene compound to an area of the body;
   d) allowing the treatment atom to react in the area of the body; and
   e) identifying and recovering the trimetallic nitride template endohedral metallofullerene compound from the body.

* * * * *

UNITED STATES PATENT AND TRADEMARK OFFICE
CERTIFICATE OF CORRECTION

PATENT NO. : 6,471,942 B1
DATED : October 29, 2002
INVENTOR(S) : Michael B. Miller et al.

It is certified that error appears in the above-identified patent and that said Letters Patent is hereby corrected as shown below:

<u>Title page</u>,
Item [54], Title, should read: -- IMAGING AND TREATMENT METHOD FOR A BODY --

<u>Column 1</u>,
Line 24, "bum" should read -- burn --.
Line 51, the formula "Er2-SC3-N@C80 (X=0-3)" should read
-- Er2-Sc3-xN@C80 (x=0-3) --.

<u>Column 4</u>,
Line 58, "Bimetallic" should read -- trimetallic --.

Signed and Sealed this

Sixteenth Day of December, 2003

JAMES E. ROGAN
*Director of the United States Patent and Trademark Office*